United States Patent [19]

Fields et al.

[11] 4,065,442

[45] Dec. 27, 1977

[54] PYROLYSIS COMPOSITIONS FROM SILVER SALTS OF POLYCARBOXYLIC ACIDS

[75] Inventors: Ellis K. Fields, River Forest; Wilford J. Zimmerschied; David A. Palmer, both of Naperville, all of Ill.

[73] Assignee: Standard Oil Company, Chicago, Ill.

[21] Appl. No.: 519,640

[22] Filed: Oct. 31, 1974

[51] Int. Cl.$^2$ ............................................. B01J 23/50
[52] U.S. Cl. ..................................... 260/78.41; 75/83; 252/476; 260/2.5 R; 260/414; 260/430; 260/348.34
[58] Field of Search ............... 260/2.5 R, 78.4 R, 430, 260/414, 78.41; 252/476

[56] References Cited

U.S. PATENT DOCUMENTS

| 2,040,782 | 5/1936 | van Peski | 252/476 |
|---|---|---|---|
| 2,446,132 | 7/1948 | Evans | 252/476 |
| 2,773,844 | 12/1956 | Carlson | 252/476 |
| 3,144,416 | 8/1964 | Hosoda | 252/476 |
| 3,775,352 | 11/1973 | Leonard, Jr. | 260/2.5 R |
| 3,779,952 | 12/1973 | Leonard, Jr. | 260/2.5 R |
| 3,943,069 | 3/1976 | Antonelli | 252/476 |
| 4,005,049 | 1/1977 | Fields | 252/476 |

Primary Examiner—Paul R. Michl
Attorney, Agent, or Firm—William C. Clarke; Arthur G. Gilkes; William T. McClain

[57] ABSTRACT

High surface area silver olefin oxide catalysts with orderly distribution of pore size are prepared by pyrolysis of silver salts of di- and polycarboxylic acids or mixtures thereof to carbon-like polymers containing silver, followed by combustion of the carbonaceous material. The resulting unsupported or supported silver catalysts are useful for oxidations, cyclizations, isomerizations, and cracking. The carbon-like polymers containing silver, before combustion of the carbonaceous material, find utility as bactericides and catalysts. Extraction of the silver yields high surface area carbon adsorbents of predetermined structure.

17 Claims, No Drawings

PYROLYSIS COMPOSITIONS FROM SILVER SALTS OF POLYCARBOXYLIC ACIDS

BACKGROUND OF THE INVENTION

The field of this invention relates to high surface area silver olefin oxide catalysts with orderly distribution of pore size, to high surface area carbon-like polymers containing silver useful as catalysts and bactericides, to high surface area carbon-like adsorbents or predetermined structure, and to the process for producing these novel silver catalysts, bactericides, and carbon adsorbents.

The use of silver as a catalyst for the oxidation of ethylene to ethylene oxide is well known, as is also the preparation of silver catalysts by the thermal decomposition of aliphatic silver salts, in particular silver oxalate but also silver formate and silver acetate. There has also been interest recently in silver catalysts with high surface areas for the oxidizing of olefins utilizing silver ketenide as an intermediate. An inherent problem with silver ketenide is that its carbon-silver bonds are often unstable, so that silver ketenide can and does decompose explosively. A search for a more stable silver catalyst intermediate led to the pyrolyzed silver salts and silver catalysts of this invention derived from aromatic and heterocyclic compounds.

The biocidal effects of silver in its free form and in the form of its salts are well-known. A controlled rate of release of silver ions into the bacteria-containing media is desirable because of the wellknown low level of silver ion which causes a biocidal effect, less than 10 parts per million in water being required. It has been found that the high surface area and ordered structures of the carbon-like polymers which contain silver produce conveniently the controlled release of the silver ions into a bacteria-containing media.

The adsorptive power of activated carbon is wellknown to be a resultant of several factors among which are pore size, total area available, and structure. The novel carbon-like polymers of this invention have high surface area and are of predetermined structure with consequent increased adsorption rate.

SUMMARY OF INVENTION

The novel silver catalysts, bactericides and adsorbents of this invention are the product of pyrolysis with or without concomitant combustion of silver salts of di-, tri- and higher polycarboxylic acids having one or more carbon-containing radical joining the silver carboxylate radicals.

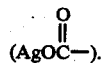

Chemical extraction of the silver from the pyrolyzed silver salts yields the carbon-like adsorbents. Such intervening carbon-containing radicals can be arylene, as in biphenylene, naphthalene, phenylene or their tri- and their higher substituted aromatic analogs and similarly substituted aromatic-like hetero-ring compounds, and mono-to-hexamethylene, vinylene, and ethynylene radicals. The preferred method is pyrolysis of such silver salts under an inert gas at the decomposition temperature which results in a sudden puffing to a novel silver-containing carbon-like polymeric product, useful as a controlled-release silver bactericide, and from which the silver can be extracted to yield the carbon-like adsorbents. Combustion of the carbon-like silver-containing polymeric products provides the novel silver catalysts. An alternative method is the subjection of such silver salts to complete combustion to result directly in the silver catalysts. High surface area, from 0.522 to 108 square meters per gram and orderly distribution of pore size characterize these silver catalysts with high activity and selectivity in oxidation, isomerization, cyclization, and cracking reactions.

DESCRIPTION OF THE PREFERRED EMBODIMENTS

Preferably, in the present invention, novel silver catalysts, bactericides and adsorbents are derived, as indicated above from di-, tri, and higher polycarboxylic acid silver salts of aromatic carboxylic acids and similar carboxylic acids of heterocyclic compounds of aromatic character. Such silver salts have the formula:

$$R(CO_2Ag)_n \qquad (I)$$

where R is an aromatic or heterocyclic ring and n is an integer 2 to 8, with preferably the carboxylic groups not ortho unless n is 3 or more.

Examples of the preferred silver salts are di-silver terephthalate, di-silver isophthalate, tri-silver trimellitate, tri-silver trimesate, tri-silver hemimellitate, tetrasilver pyromellitate, tetra-silver mellophanate, penta-silver benzenepentacarboxylate, hexa-silver melitate, di-silver salts of naphthalene 1,3-, 1,4-, 1,5-, 1,6-, 1,7-, 1,8-, 2,4-, 2,6-, and 2,7-dicarboxylic acids, tetra-silver 1,4,5,8-naphthalene tetracarboxylate, octa-silver naphthalene octa-carboxylate, di-silver pyridine 2,4-, 2,5-, 2,6-, 3,5-, and 3,6-dicarboxylates, di-silver thiophene-2,5-dicarboxylate, and the silver salts of di-, tri- and tetracarboxylic acids of anthracene, anthraquinone, phenanthrene, chrysene, perylene, quinoline, isoquinoline, phenanthridine, benzothiophene (thianaphthene), dibenzothiophene, benzofuran, and dibenzofuran.

Other silver salt sources of the present invention, silver catalysts, bactericides and carbon adsorbents are the silver salts of polycarboxylic acids of formula II, III, IV, and V which follow.

Silver salts of formula II:

are those wherein R and R' are the same or different aryl or heterocyclic radicals, n and m are integers 1–4, and X is a divalent atom or radical selected from the group —O—, —S—, —Se—, —NH—,

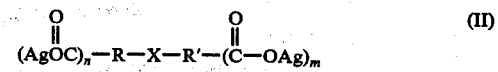

—SO$_2$—, —N=N—, —CH=CH—, or C≡C—. Examples of these silver salts are di-silver diphenylether-4,4'dicarboxylate, di-silver methylenedibenzoate, di-silver diphenylsulfone-4,4'-dicarboxylate, di-silver benzophenone-4,4'-dicarboxylate, tetra-silver benzophenone-3,3',4,4'-tetracarboxylate, di-silver stilbene-4,4'-dicarboxylate, di-silver diphenylacetylene-4,4'-dicarboxylate, and di-silver azobenzene-3,3'-dicarboxylate.

The silver salts of formula III-IV used are those of structures:

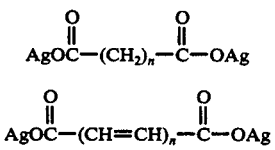

where n is an integer 1 to 6. Representatives of silver salts of formula III-IV are di-silver malonate, di-silver succinate, di-silver adipate, di-silver fumarate, di-silver 1,3-butadiene-1,4-dicarboxylate, and di-silver 1,3,5-hexatriene-1,6-dicarboxylate.

Silver salts of formula V:

$$\underset{AgOC-C_6H_nX_m-COAg}{\overset{O\quad\quad\quad O}{\overset{\|\quad\quad\quad\|}{}}} \quad\quad V$$

where X is a halogen selected from the group consisting of fluorine, chlorine, bromine, and iodine, n and m being whole numbers from 0 to 4 and n plus m totaling 4. Examples of these silver salts of formula V are di-silver 2,5-dibromoterephthalate, di-silver 2,5-dichloroterephthalate, di-silver tetraiodophthalate, di-silver tetrachloroterephthalate, di-silver tetrabromoterephthalate, di-silver tetrafluoroterephthalate, di-silver 4-bromoisophthalate, di-silver 4,6-dibromoisophthalate, and di-silver tetrachlorophthalate.

The novel silver catalysts, bactericides and adsorbents of this invention have large surface areas and orderly distribution of pore size, with predetermined structure. The preferred method of preparing such novel compositions is by pyrolyzing silver salts of di- and poly-carboxylic acids at temperatures of 200°–500° C, utilizing a suitable source of heat such as a hot plate or a furnace, for 1–60 minutes under a blanket of inert gas such as nitrogen, argon or helium, and, alternatively, in limited air, to produce carbon-like polymers containing silver. These become evident with a sudden puffing-up at the decomposition temperatures. Combustion of the carbon-like polymers, which contain silver, in the presence of, alternatively, added oxygen, air, and mixtures of nitrogen and oxygen at 20°–500° C yields the silver catalysts. The carbon-like polymers which contain silver may be used immediately as catalysts and bactericides. Chemical extraction of the silver yields the carbon-like adsorbents.

If a furnace is used, the pyrolysis reaction may be run conveniently by spreading the powdered silver salt as a thin layer along the length of a Pyrex, Vycor, quartz, or stainless steel tube which is then heated to obtain the pyrolysis products. Should the silver catalysts be required, the carbon-like polymers containing silver may be cooled to 20° C under nitrogen or hydrogen, then treated with oxygen or oxygen-containing mixtures. The organic material is allowed to burn off by being heated to the temperature required for such oxidation, preferably at the lowest temperature at which oxidation occurs to avoid unnecessary sintering of the desired silver catalyst. Such temperatures usually will be within the range of 100°–200° C.

A second method of preparing such catalysts without the intervening availability of the carbon-like polymers is the combustion of the aforementioned classes of silver salts in air utilizing a suitable source of heat such as a hot plate or a furnace to burn off the carbon-like polymer which forms during combustion, preferably at the lowest oxidation temperatures at which oxidation occurs to avoid sintering.

Surface-area analysis and pore-size distribution determinations were made using low temperature nitrogen or krypton absorption with a Digisorb 2500 surface analysis instrument in conjunction with a computer using well-known techniques. A typical determination via a computer printout showed pore size, pore volume, total surface area, as well as percent volume and surface area associated with any given pore size.

The silver salts may first be admixed with inert material supports such as alumina, silica, silica-alumina, or keiselguhr before being pyrolyzed to their decomposition temperatures. The product of the combustion or organic material left by pyrolysis is a supported active catalyst of high surface area and uniform pore size.

In order to facilitate a clear understanding of the invention, the new compositions of matter and the combustion processes by which they are achieved, the following specific embodiments are described in detail.

EXAMPLE I

Silver trimellitate, 25 grams, was placed in a crystallizing dish on a hot plate. A funnel connected by rubber tubing to a nitrogen supply was inserted over the dish to maintain a nitrogen purge. The crystallizing dish was heated until a vigorous decomposition occurred. For silver trimellitate a temperature of about 310° C is required. Decomposition was evidenced by a sudden puffing-up of the contents of the crystallizer dish as the color changed from a light beige to black. Heating was stopped and the nitrogen purge was maintained while the dish and contents cooled to room temperature.

Three grams of the black product were placed in a ⅜ inch glass tube and placed in an electrically heated furnace. A mixture of 3.3% oxygen in nitrogen was passed through the tube as the temperature of the furnace was slowly raised to 425° F. After 27 hours the color of the catalyst had become greyish brown and there had been some shrinkage in volume due to the oxidation of the carbonaceous decomposition products. The cooled product weighed 2.5 grams.

EXAMPLE II

The di-silver salt of terephthalic acid, 3.8 grams and 0.01 mole, which decomposes at 420° C, was placed as a thin layer of powdered silver salt along the length of a quartz tube and heated in a furnace under nitrogen at 450° C for 1 minute. Carbon dioxide evolved and the white solid became black. It was cooled under nitrogen for 30 minutes. The carbon-like product weighted 2.6 grams and analyzed: carbon 15.9%, hydrogen 0.6%, silver 79.7%. The product combusted at 70° C in the presence of air and yielded the silver metal catalyst whose surface area was 0.566 square meters/gram.

EXAMPLE III

The di-silver salt of isophthalic acid, 3.8 grams and 0.01 mole, which decomposes at 350° C, was placed as a thin layer of powdered silver salt along the length of a Pyrex tube and heated in a furnace under nitrogen at 380° C for one minute. Carbon dioxide evolved and the white solid became black. It was cooled under nitrogen for 30 minutes to 25° C. The carbon-like product weighed 3.0 grams and analyzed: carbon 18.7%, hydrogen 0.6%, silver 77.3%. The product combusted in air at 150° C to yield the silver metal catalyst with surface area 0.522 square meters/gram.

EXAMPLE IV

The tri-silver salt of trimellitic acid, 3.15 grams and 0.005 moles, which decomposes at 310° C, was placed as a thin layer of powdered silver salt along the length of a quartz tube and heated in a furnace under nitrogen at 350° C for one minute. Carbon dioxide evolved and the white solid became black. It was cooled under nitrogen for 30 minutes to 25° C. The carbon-like product weighed 2.35 grams and analyzed: carbon 16.9%, hydrogen 0.7%, silver 78.1%. The product combusted in air at 200° C to yield the silver metal catalyst with surface area 0.67 square meters/gram.

EXAMPLE V

The tetra-silver salt of pyromellitic acid, 3.41 grams and 0.005 moles, which decomposes at 330° C, was placed as a thin layer of powdered silver salt along the length of a quartz tube and heated in a furnace under nitrogen at 350° C for 2 minutes. Carbon dioxide evolved and the white solid became black. It was cooled under nitrogen for 30 minutes to 25° C. The carbon-like product weighed 2.55 grams and analyzed: carbon 12.1%, hydrogen 0.3%, silver 82.3%. The product combusted in air at 225° C to yield the silver metal catalyst with surface area 0.78 square meters/gram.

EXAMPLE VI

The hexa-silver salt of mellitic acid, 3.3 grams and 0.003 moles, which decomposes at 260° C, was placed as a thin layer of powdered silver salt along the length of a quartz tube and heated in a furnace under nitrogen for two minutes at 300°C. Carbon dioxide evolved and the white solid became black. It was cooled under nitrogen for 30 minutes to 25° C. The carbon-like product weighed 1.1 grams and analyzed: carbon 9.0%, hydrogen 0.2%, silver 85.3%. The product combusted in air at 250° C to yield the silver metal catalyst with pore size 15-600 A in diameter evenly distributed and surface area 22.76 square meters/gram.

EXAMPLE VII

The tri-silver salt of trimesic acid, 3.15 grams and 0.005 moles, which decomposes at 360° C, was placed as a thin layer of powdered silver salt along the length of a quartz tube and heated in a furnace under nitrogen for one minute at 400° C. Carbon dioxide evolved and the white solid became black. It was cooled under nitrogen for 30 minutes to 25° C. The carbon-like product weighed 2.15 grams and analyzed: carbon 17.5%, hydrogen 0.6%, silver 79.9%. The product combusted in air at 275° C to yield the silver metal catalyst with 79.7% of the pores being 15-28 A in diameter and surface area 108 square meter/gram.

EXAMPLE VIII

The di-silver salt of fumaric acid, 9.9 grams and 0.03 mole, which decomposes at 320° C, was placed as a thin layer of powdered silver salt along the length of a quartz tube and heated in a furnace under nitrogen for one minute at 350° C. Carbon dioxide evolved and the white solid became black. It was cooled under nitrogen for 30 minutes to 25° C. The carbon-like product weighed 7.3 grams and analyzed: carbon 6.6%, hydrogen 0.3%, silver 90.0%. The product combusted at 350° C to yield the silver catalyst with surface area 2.53 square meters/gram.

EXAMPLE IX

The di-silver salt of pyridine-3,5-dicarboxylic acid, 7.94 grams and 0.02 moles, which decomposes at 318° C, was placed as a thin layer of powdered silver salt along the length of a quartz tube and heated in a furnace under nitrogen for two minutes at 350° C. Carbon dioxide evolved and the white solid became black. It was cooled under nitrogen for 30 minutes to 25° C. The carbon-like product weighed 6.2 grams and analyzed: carbon 15.5%, hydrogen 0.9%, nitrogen 4.7%, silver 77.0%. The product combusted in air at 250° C to yield the silver catalyst with surface area 1.17 square meters/gram.

EXAMPLE X

The tetra-silver salt of benzophenone-3,4,3',4'-tetracarboxylic acid was prepared in quantitative yield by adding a solution of 35.8 grams (0.1 mole) of benzophenone 3,4,3',4'-tetracarboxylic acid in 0.4 mole of aqueous sodium hydroxide to a solution of 0.4 mole of silver nitrate in water with stirring. The white precipitate was collected on a filter, washed thoroughly with water and dried, first in air and under a partial vacuum at 90° C.

The aforesaid tetra-silver salt, 3.14 grams and 0.004 mole, which decomposes at 291° C, was placed as a thin layer of powdered silver salt along the length of a quartz tube and heated in a furnace under nitrogen for two minutes at 320° C. Carbon dioxide evolved and the white solid became black. It was cooled under nitrogen for 30 minutes to ambient temperatures. The carbon-like product weighed 2.44 grams and anaylzed: carbon 23.6%, hydrogen 0.9%, silver 67.5%. The product combusted in air at 250° C to yield the silver catalyst with surface area 1.02 square meters/gram.

EXAMPLE XI

The di-silver salt of phthalic acid, 7.6 grams and 0.02 moles, which decomposes at 275° C, was placed as a thin layer of powdered silver salt along the length of a quartz tube and heated in a furnace under nitrogen for 5 minutes at 300° C. Carbon dioxide evolved and the white solid became black. It was cooled under nitrogen for 30 minutes to 25° C. The carbon-like product weighed 6.1 grams and analyzed: carbon 23.4%, hydrogen 0.9%, silver 74.1%. The product combusted in air at 140° C to yield the silver catalyst with surface area 22.76 square meters/gram.

EXAMPLE XII

The di-silver salt of thiophene-2,5-dicarboxylic acid, 7.72 grams and 0.02 moles, which decomposes at 315° C, was placed as a thin layer of powdered silver salt along the length of a quartz tube and heated in a furnace under nitrogen for 5 minutes at 325° C. Carbon dioxide evolved and the white solid became black. It was cooled under nitrogen for 30 minutes to 25° C. The carbon-like product weighed 5.77 grams and analyzed: carbon 15.4%, hydrogen 0.6%, sulfur 4.4%, silver 79.6%. The product combusted in air at 130° C to yield the silver catalyst with 37.09% of the pores 15-25 A in diameter and surface area 19.3 square meters/gram.

EXAMPLE XIII

Utility of such silver catalysts was demonstrated by selective oxidation of olefin to an epoxide. The silver catalyst resulting from pyrolyzed di-silver trimellitate prepared as taught in Example I was utilized.

The silver catalyst, 1.5 grams (4 ml) was charged into a stainless steel reactor of ⅜ inches diameter and 17 inches in length. The reactor was electrically heated and operated at a pressure of 200 psig (14.06 kg/sq. cm.). A feed gas mixture consisting of 4.81 mole % oxygen, 8.17 mole % ethylene and 87.0 mole % nitrogen was passed over the catalyst at a flow rate of 9000 ft³/hour/ft³ catalyst. The product was analyzed using in-line gas chromatography.

Excellent low temperature activity was demonstrated by the silver catalyst of Example I. Four runs were made at temperatures under 250° C. To achieve 10% ethylene conversion with good selectivity, 56.5%, a temperature of only 236.7° C was required.

A commercial catalyst, Engelhard EOS-8, under the same conditions of operation required a temperature of 273.3° C to achieve approximately the same ethylene conversion, 9.2%, with somewhat lower selectivity, 47%. Table I shows data obtained on ethylene conversion and selectivity to ethylene oxide for this catalyst as well as the aforementioned commercial catalyst under the conditions given.

TABLE I

Effect of Operating Temperature on the Conversion of Ethylene and the Selectivity to Ethylene Oxide

| Run No. | Temp. °C. | Catalyst | Ethylene Conversion, % | Selectivity % Ethylene Oxide | Aldehyde |
|---|---|---|---|---|---|
| 1 | 208.9 | Example I | 4.6 | 67.0 | 7.3 |
| 2 | 224.4 | Example I | 7.2 | 55.7 | 5.0 |
| 3 | 236.7 | Example I | 10.1 | 56.5 | 6.2 |
| 4 | 244.4 | Example I | 24.3 | 44.7 | 1.0 |
| 5 | 273.3 | Commercial Engelhard Catalyst (EOS-8)[2] | 9.2 | 47.3 | 9.5 |

[1]Silver catalyst described in Example I (1.5 grams of catalyst, volume of 4.0 ml)
[2]For this example, 4 grams of catalyst were used, which had a volume of 3.3 ml.

EXAMPLE XIV

The low temperature activity of a silver catalyst prepared from the silver salt of a dicarboxylic aromatic acid using the method of simple combustion demonstrates the novelty and utility of such catalysts prepared by such method, which illustrates that the utility and novelty of these catalysts is not limited by the method of preparation.

The di-silver salt of isophthalic acid, 7.6 grams and 0.02 mole, which decomposes at 350° C, was heated in a crystallizing dish on a hot plate in air for two minutes at 400° C. A carbon-like polymer formed initially and then burned off quickly to give 4.28 grams of silver catalyst.

Four grams of this silver catalyst were placed in a ½ inch glass tube and placed in an electrically heated furnace. A mixture of ten volumes of ethylene and one volume of air was passed over this silver catalyst at 200°-220° C, 114 psi. (8.01 kg/sq. cm.), with a two second contact time. Results were: ethylene conversion 3.7%, selectivity to ethylene oxide 49.7%, selectivity to acetaldehyde 6.7%, selectivity to carbon dioxide 43.6%. Under identical conditions, a commercial silver catalyst, Engelhard EOS-8, gave 3.5% conversion with 100% selectivity to carbon dioxide.

EXAMPLE XV

The cyclization and isomerization activity of silver catalysts prepared from the di-silver salt of terephthalic acid demonstrates the versatile utility of such catalysts. The use of these silver catalysts conjunctively with suitable support materials as silica gel demonstrates that the cyclization and isomerization activity of these silver catalysts remains through support material are utilized.

The di-silver salt of terephthalic acid, 10 grams, which decomposes at 420° C, was thoroughly mixed with 33 grams of silica gel, 3–9 mesh. The salt and the gel were ground together with mortar and pestle, then shaken together in a jar. The mix was charged into a stainless steel reactor of ⅜ inches diameter and 17 inches in length. The reactor was electrically heated. The mixture was slowly heated in the reactor to 470° C under nitrogen, flowing at 100 cc/min. The mixture was kept at 470° C for ten minutes, then allowed to cool to 400° C.

Hexene-1, 21.64 ml. and 0.2 mole was passed over the catalyst in the reactor. Contact time was 50 seconds. The product, 18 ml, consisted of 98.5% cyclohexane, 0.3% hexene-2 and hexene-3, and 1% benzene.

The high selectivity, 98.5%, and conversion, 88.4%, of hexane-1 to cyclohexane demonstrates the utility of these silver catalysts when used conjunctively with suitable support materials.

EXAMPLE XVI

The cyclization and isomerization activity of the carbon-like polymers containing silver prepared from the di-silver salt of isophthalic acid demonstrates the versatile utility of these novel compositions in that they are useful as catalysts.

The di-silver salt of isophthalic acid, 15.0 grams and 0.04 mole, which decomposes at 350° C, was placed as a thin layer of powdered silver salt along the length of a Vycor reactor tube and heated in a furnace under nitrogen at 400° C for two minutes. Carbon dioxide ($CO_2$) evolved and a carbon-like polymer containing silver became evident with a sudden puffing up. Combustion of the silver salt subsided with the formation of the polymer and with cessation of evolution of $CO_2$. At 400° C, 22 milliliters (0.2 mole) of pentene-1 was passed through this catalyst with a contact time of 10.3 seconds. The condensate, 19 milliliters, was analyzed. Results were pentene-1 conversion 2.0%, selectivity to n-pentane 18.4%, selectivity to trans-pentene-2 15.3%, selectivity to cis-pentene-2 10.1%, selectivity to 2-methylbutene-2 20.5%, selectivity to higher olefin and diolefins 35.8%. The original sample of pentene-1 when run at 400° C for 10.3 seconds through a tube but without a catalyst showed only a trace of conversion to n-pentane. No other isomers were detected in the sample run without a catalyst. The analyses were by gas chromatography.

EXAMPLE XVII

The utility of the pyrolysis method in retaining the heteroatoms in the carbon-like polymers containing silver is demonstrated in the following example.

The di-silver salt of azobenzene-3,3'-dicarboxylic acid, 9.68 grams and 0.02 moles, which decomposes at 330° C, was placed as a thin layer of powdered silver salt along the length of a Vycor tube and heated in a furnace under nitrogen at 400° C for one minute. Carbon dioxide ($CO_2$) evolved and a carbon-like polymer containing silver became evident with a sudden puffing up. Heating was stopped and the nitrogen purge was maintained while the tube and contents cooled to room temperature. Theoretical loss of $CO_2$ was 1.84 grams. Actual loss of weight upon pyrolysis was 2.3 grams. Calculated analysis of the pyrolyzed product as 3,3'-disilver azobenzene was carbon 36.3%, hydrogen 2.0%, nitrogen 7.1%, silver 54.6%. The resulting carbon-like-polymer analysis was carbon 27.9%, hydrogen 1.4%, nitrogen 4.1% and silver 65.5%. The analysis indicates that over one-half the polymeric product retains the azo nitrogen in its structure.

EXAMPLE XVIII

In a similar procedure to that used in Example XVII, the di-silver salt of azobenzene-4,4'-dicarboxylic acid was pyrolyzed. The salt was prepared in 83 mole % yield by reacting 314 grams, 1.0 mole, di-sodium azobenzene-4,4'-dicarboxylate with two moles of silver nitrate, collecting the insoluble silver salt, followed by washing and drying of the salt. The di-silver salt, 9.68 grams and 0.02 moles, which decomposes at 365° C, was placed as a thin layer of powdered silver salt along the length of a Vycor reactor tube and heated in a furnace under nitrogen at 400° C for two minutes. Carbon dioxide ($CO_2$) evolved and a carbon-like polymer containing silver occurred with a sudden puffing up. Combustion of the silver salt subsided with the formation of the polymer and with cessation of evolution of $CO_2$. Heating was stopped and the nitrogen purge was maintained while the tube and contents cooled to room temperature. The sample analyzed: carbon 14.2%, hydrogen 0.7%, nitrogen 2.2%, and silver 82.4%.

EXAMPLE XIX

The di-silver of thiophene-2.5-dicarboxylic acid was prepared in 96 mole % yield by reacting 34.4 grams, 0.2 moles, of disodium thiophene-2,5-dicarboxylate in 500 milliliters of water with 0.4 moles of silver nitrate in 500 milliliters of water, collecting the precipitated silver salt on a filter, followed by washing and drying of the salt. The di-silver salt, 7.75 grams, and 0.02 moles, which decomposes at 315° C, was placed as a thin layer of powdered silver salt along the length of a Vycor reactor tube and heated in a furnace under nitrogen at 350° C for two minutes. Carbon dioxide ($CO_2$) evolved with a sudden puffing up. Combustion of the silver salt subsided with the formation of the polymer and with cessation of evolution of $CO_2$. Heating was stopped and the nitrogen purge was maintained while the tube and contents cooled to room temperature. The calculated loss of $CO_2$ for 0.04 moles $CO_2$ was 1.76 grams. Actual weight loss was 1.95 grams. The resulting carbon-like polymer containing silver analyzed: carbon 15.4%, hydrogen 0.6%, sulfur 4.4%, and silver 79.7%.

EXAMPLE XX

The utility of the carbon-like polymers containing silver as bactericides was demonstrated by the carbon-like polymers of Examples III and VII. One gram each of the carbon-like polymers prepared in these two examples, before final combustion to yield the silver catalysts of the same examples, was stirred separately with 100 milliliters of sterile distilled water for ten minutes. The polymer samples from Examples III and VII were then extracted from the distilled water by filtration, dried, and weighed. There was no significant weight loss, less than 0.1 milligram, in either sample. Bacterial cultures were prepared using the distilled water filtrate, with four grams of Eastman purified pigskin gelatin, two grams beef bouillon, and two grams sucrose. The bacterial cultures were placed in Petri dishes. Control culture media were prepared in the same manner, using sterile distilled water which had not been exposed to the polymer samples of Examples III and VII, and placed in Petri dishes. All dishes were exposed to adventitious bacteria and fungi by being left open to air for two hours. After six days at 25° C, the dishes were rated for growth of bacterial and fungi colonies. A +5 is luxuriant growth with the plate completely covered with colonies of microorganisms. A —0— is no growth. The three control dishes showed +5 in each case. The broth from Examples III and VII showed —0— in each case, or no growth.

EXAMPLE XXI

The utility of the carbon-like polymers after extraction of the silver to produce adsorbents of high surface area, low density and ordered structure is demonstrated in the following example.

Tri-silver trimesate, 10.62 grams and 0.02 mole, which decomposes at 360° C, was placed as a thin layer of powdered silver salt along the length of a Vycor reactor tube and heated in a furnace under nitrogen at 400° C for two minutes. Carbon dioxide evolved ($CO_2$) and a carbon-like polymer containing silver became evident with a sudden puffing up. Heating was stopped and the nitrogen purge was maintained while the tube and contents cooled to room temperature. Theoretical weight loss of $CO_2$ was 2.76 grams and 0.06 moles. Actual weight loss was 2.8 grams. The cooled product was digested with 175 milliliters of 20% nitric acid for ten minutes at 40°-50° C. The product was collected upon a filter, washed and air-dried. The air-dried polymer weighed 23 grams. The product was dried under vacuum of 160 mm Hg and 110° C for six hours, at which time the sample weighed 1.1 grams. Density of the sample was 0.0072 and surface area was 1082 square meters/gram. Uptake of total organic carbon (TOC) in simulated municipal waste water was 415 milligrams/gram. A commercial activated charcoal used industrially for gas adsorption and decolorizing, with a density of 0.0317 and a surface area of 1022 square meters/gram demonstrated a TOC of 247 milligrams/gram.

EXAMPLE XXII

Tri-silver trimellitate, 10.62 grams and 0.02 mole, which decomposes at 310° C, was pyrolyzed in the method of Example XXI at 400° C for 5 minutes under nitrogen, cooled, and digested with 175 milliliters of 20% aqueous nitric acid at 40–50° C for 15 minutes. The carbon-like polymer was collected on a filter, washed with water and air-dried. It weighed 25 grams. After it was dried in a vacuum oven at 160 mm Hg and 105° C for 12 hours, it weighed 0.9 grams. Density was 0.0084, surface area was 950 square meters/gram. TOC was 385.

EXAMPLE XXIII

Di-silver isophthalate, 7.6 grams and 0.02 mole, which decomposes at 350° C, was pyrolyzed in the method of Example XXI at 400° C for 5 minutes under nitrogen, cooled to 20° C under nitrogen, and digested with 50 milliliters of 70% nitric acid, specific gravity of 1.42, at 40°-50° C for ten minutes. The carbon-like polymer was collected on a filter, washed and dried in a vacuum of 160 mm Hg. and 110° C for 12 hours. It weighed 1.42 grams and analyzed: carbon 76.0%, hydrogen 2.9%, nitrogen 6.8% and oxygen 14.3%. Calculated analysis for $C_{12}H_7NO_2$ is: carbon 73.2%, hydrogen 3.6%, nitrogen 7.1%, and oxygen 16.2%. Density was 0.0096, surface area was 920 square meters/gram. TOC was 365.

EXAMPLE XXIV

The di-silver salt of 2,5-dichloroterephthalic acid was prepared in quantitative yield from an aqueous solution of 1 mole di-sodium 2,5-dichloroterephthalate added to an aqueous solution of 2 moles of silver nitrate, by filtering, washing, and drying. The salt decomposes at 298° C.

Di-silver 2,5-dichloroterephthalate, 13.47 g., 0.03 mole, was heated under nitrogen at 305° C for 10 minutes. The resulting voluminous brown product was cooled to 25° C under nitrogen, extracted with four 50 ml. portions of 4N sodium thiosulfate solution to dissolve silver chloride, washed thoroughly with distilled water, and dried in air. It weighed 53.6 grams and was apparently dry to the touch. After 16 hours in a vacuum oven at 100° C, the product weighed 5.0 g. It evidently can hold over 10X its own weight of liquid.

The product was analyzed by a Digisorb analyzer. It had a surface area of 390 square meters per gram, with 90% of its pores 20-22A in diameter, a surprisingly uniform small pore size.

EXAMPLE XXV

DI-silver 2,5-dibromoterephthalate, 10.76 grams, 0.02 mole, 303° C decomposition temperature, was pyrolyzed at 310° C under nitrogen for 5 minutes. The resulting exceedingly voluminous brown product was cooled under nitrogen to 25° C, extracted with 4N sodium thiosulfate to remove silver bromide, washed thoroughly with water, and dried in air. It weighed 16.7 g. and appeared dry to the touch. After being heated in a vacuum oven at 100° C for 16 hours, the product weighed 0.6 g. It is capable apparently of holding 27.8 times its own weight of liquid. The dry product had a surface area of 863 square meters/gram and pores of which 83% were 15-30A in diameter.

What is claimed is:

1. A process for producing high surface area compositions with predetermined structure which comprises pyrolyzing at a decomposition temperature within the range of from about 200° to 500° C polysilver salts of polycarboxylic acids containing two to eight carboxyl groups comprising at least one member selected from the group consisting of aromatic polycarboxylic acids and heterocyclic polycarboxylic acids.

2. The pyrolysis product produced by the process of claim 1.

3. The process of claim 1 wherein the said silver salts of polycarboxylic acids are pyrolyzed under an inert gas.

4. The process of claim 3 wherein the silver component of the pyrolyzed composition is chemically removed.

5. The carbonaceous product produced by the process of claim 4.

6. The pyrolysis compositions of claim 1 prepared by pyrolyzing said silver salts at temperatures from about 200° to 500° C under inert gases to decompose said salts to silver and carbon-like polymers which are subsequently removed by combustion at temperatures from 20 to 500° C.

7. The process of claim 3 wherein the carbonaceous material is removed from the pyrolyzed composition by oxidation in an oxygen-containing gas.

8. The silver product produced by the process of claim 7.

9. The process of claim 1 wherein the polysilver salt comprises the disilver salt of azobenzene-4,4'-dicarboxylic acid.

10. The process of claim 1 wherein the polysilver salt comprises the disilver salt of thiophene-2,5-dicarboxylic acid.

11. The process of claim 4 wherein the silver component of the pyrolyzed composition is chemically removed with nitric acid.

12. The process of claim 1 wherein the polysilver salt comprises the polysilver salts or aromatic polycarboxylic acids.

13. The process of claim 1 wherein the polysilver salt comprises the disilver salt of 2,5-dibromoterephthalic acid.

14. The process of claim 1 wherein the polysilver salt comprises the polysilver salts of trimellitic acid.

15. The process of claim 1 wherein the polysilver salt comprises the polysilver salts of trimesic acid.

16. The process of claim 1 wherein the said polysilver salts of polycarboxylic acids are pyrolyzed while supported on an inert material selected from the group consisting of alumina, silica, silica-alumina and kieselguhr.

17. The pyrolysis compositions of claim 8 containing inert material as support.

* * * * *

UNITED STATES PATENT OFFICE
CERTIFICATE OF CORRECTION

Patent No. 4,065,442  Dated December 27, 1977

Inventor(s) Ellis K. Fields et al.

It is certified that error appears in the above-identified patent and that said Letters Patent are hereby corrected as shown below:

Column 1, line 10, "or" should be -- of --.

Column 4, line 14, "or" should be -- of --.

Column 8, line 5, "remains through" should be "remains though"

Column 11, line 30, "DI-silver" should be "Di-silver"

Column 12, line 34 "salts or aromatic" should be "salts of aromatic"

Signed and Sealed this

Seventh Day of November 1978

[SEAL]

Attest:

RUTH C. MASON
Attesting Officer

DONALD W. BANNER
Commissioner of Patents and Trademarks